United States Patent
Corvalán et al.

(10) Patent No.: US 11,746,387 B2
(45) Date of Patent: Sep. 5, 2023

(54) NON-INVASIVE DETECTION OF GASTRIC CANCER BY DETECTING THE METHYLATION OF REPRIMO-LIKE IN THE BLOOD

(71) Applicant: PONTIFICIA UNIVERSIDAD CATOLICA DE CHILE, Santiago (CL)

(72) Inventors: Alejandro Corvalán, Santiago (CL); Alejandra Alarcón, Santiago (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 0 days.

(21) Appl. No.: 17/252,571

(22) PCT Filed: Jun. 20, 2018

(86) PCT No.: PCT/CL2018/050047
§ 371 (c)(1),
(2) Date: Dec. 15, 2020

(87) PCT Pub. No.: WO2019/241899
PCT Pub. Date: Dec. 26, 2019

(65) Prior Publication Data
US 2021/0254175 A1    Aug. 19, 2021

(51) Int. Cl.
*C12Q 1/6886* (2018.01)

(52) U.S. Cl.
CPC ..... *C12Q 1/6886* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

2013/0022974 A1* 1/2013 Chinnaiyan .......... C12Q 1/6886
                                                                 435/6.11
2014/0206574 A1   7/2014 Chapman

FOREIGN PATENT DOCUMENTS

| WO | 2012/174256 | 12/2012 |
| WO | 2015/115544 | 8/2015 |
| WO | 2016/205971 | 12/2016 |

OTHER PUBLICATIONS

Ehrlich et al. (2002 Oncogene vol. 21 p. 5400) (Year: 2002).*
Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
International Search Report issued in International Application No. PCT/CL2018/050047, dated Nov. 21, 2018, 8 pages with translation.
Lin, et al., "Reprimo-like is a p53 Responsive Gene Whose Promoter Methylation May Predict for Radiation Responsiveness in Pancreatic Cancer", International Journal of Radiation Oncology Biology Physics, 2010, 78(3), S129.
Wichmann, et al., "Evolutionary history of the reprimo tumor supressor gene family in vertebrates with a description of a new reprimo gene lineage", Gene, 2016, 591:245-254.
Figueroa, et al., "Reprimo tissue-specific expression pattern is conserved between zebrafish and human", PLoS One 2017; 12(5): e0178274, 18 pages.
Kalnina, et al., Emerging blood-based biomarkers for detection of gastric cancer Worid Journal of Gastroenterology, Nov. 7, 2015; 21(41), 11636-11653.

* cited by examiner

*Primary Examiner* — Katherine D Salmon
(74) *Attorney, Agent, or Firm* — Hamre, Schumann, Mueller & Larson, P.C.

(57) ABSTRACT

The invention aims at a non-invasive method of early diagnosis of gastric cancer, using as a biomarker the levels of methylation of the DNA sequence of the promoter of the Reprimo-like gene in plasma. The inventors have established the utility of Reprimo-like as a biomarker, and especially as a biomarker for the early detection of gastric cancer, since they have determined that Reprimo-like is consistently silenced in gastric cancer, both in incipient and advanced stages. This silencing is given by methylation of its promoter region, which is detectable in plasma samples, allowing us to measure it as a liquid biopsy in a non-invasive, fast and inexpensive way.

2 Claims, 1 Drawing Sheet

Specification includes a Sequence Listing.

SEQUENCE LISTING

<160> NUMBER OF SEQ ID NOS: 3

<210> SEQ ID NO 1
<211> LENGTH: 5000
<212> TYPE: DNA
<213> ORGANISM: Homo sapiens

<400> SEQUENCE: 1

| | | | | | | |
|---|---|---|---|---|---|---|
| gaggacactc | aagcagcacc | atggagaggt | ccgatggcga | ggaacagagg | atcccctgc | 60 |
| cgacagccaa | tgaggaacag | gcctcctgcc | aacagccgtg | taaggggtca | ccttggaagc | 120 |
| caatggcccc | tccctggtca | ggcttttaca | tgactgcagt | cctggccaac | atcctgacgg | 180 |
| caacctcatg | agagaccttg | agccagagcc | acccacctaa | gctgcttata | ggttcctggc | 240 |
| cctcagaaat | cacatgagat | cataaatgtt | tgctcaattt | gagatatttg | tgatgtagca | 300 |
| ataaataaca | aacacactta | cctttcaggg | ttattatgag | aattaagagt | taatacacat | 360 |
| caaactacaa | ccaaacttgc | tgggaccaga | ggctcaagaa | agggcagaca | gggccgggtg | 420 |
| cagtggctca | tgcctgtaat | cccaatactt | tgggaggccg | aggcaggtgg | atcatctgag | 480 |
| gtcaggagtt | cgagaccagc | tggccaacat | ggtgaaaccc | tgtgtctact | aaaaatacaa | 540 |
| aaattagcca | ggcatggtgg | cggacacctg | taatcccagc | tactcgggag | gctgaggcag | 600 |
| gcctcacttg | aacctgagag | ctggaggctg | aagtgagcag | agatcatgcc | accgcactcc | 660 |
| agcctgggtg | acatagcgag | actccgtctc | aaaaaaaaaa | aaaaaaaaaa | aaaagaaga | 720 |
| aagggcagac | agaaaccaca | gaaggaggag | tggttagcta | ggtccaggcc | agatggggtc | 780 |
| ctgctcctga | cgtggatggt | tctgggagac | caaatatgca | aatagacaat | ggccagacca | 840 |
| catattaaaa | tagaactctg | cccccaaacc | tacagcacca | gcccaggaag | ccaacgaaca | 900 |
| accctgcag | caatcagccc | caaatggcca | ggacttgatg | gtaactgaca | gcttccctaa | 960 |
| ttttgttccc | actttcaatg | caggacaaac | cggagaaagc | caaatatgct | cccctaacca | 1020 |
| attacttagg | atgcccctct | tctaatgagc | ccaactgtag | ctttcctgca | ccaccaacag | 1080 |
| gacgtacctg | aagccttctc | cttttttccgc | tataaagcct | tcccctcggc | ctgcctttga | 1140 |
| gtctccatga | aaagcaagtg | acagtggctg | cctcccttac | tgtaacaagc | tctgaataaa | 1200 |
| cagcctttgc | ttgctctcat | ttgagtggtc | tttgtttaca | tccacaagcc | caaggtctct | 1260 |
| ctccccctcc | ctgctcccag | gtcaaagatg | tcttttttccc | tccccagcac | ctcccccagg | 1320 |
| gatgatggga | gagagggga | cggggataat | gaagagcgtg | gctttggaac | aggacagatc | 1380 |
| tgggctgaaa | ttctggctct | gatgcttaac | tagctgcgtg | atcttaagta | agtcaattaa | 1440 |
| acagtcagtg | ccgctgtttc | ctcatgtcaa | ggggacagtc | cagcagaacc | caaaggctgg | 1500 |
| tgtgagagaa | ttcagggagg | taatgtattt | aatgcactgg | gcatgtaata | gatgcttaat | 1560 |
| aaaggaaagg | tcagccatca | tgtcagcctc | ctcacaactc | gctggagtgg | gcagggcccc | 1620 |
| attctgcatc | ctcactcacc | ccacccctttt | cctttacatc | aggcagtctg | acttcagctg | 1680 |
| gatgcaatca | aggtacggac | tccaagtcca | gggtatagca | aaagccaggg | gttggtttca | 1740 |
| gacaaaggat | ataactgagc | atttctctac | agaaatccaa | ttgggccaaa | gcagaggaca | 1800 |
| gaatgttcgg | gccagacacc | tgctggactc | cctgttctat | cctggctcca | aggggtgatc | 1860 |
| agggcagggg | agactcttgc | cctgaaaact | gcatgccttt | gcgccaggcc | agcttttccca | 1920 |
| ggactgagga | gcttgagcca | ggttgtttcc | caatctgggg | tgcctatgtg | tgcctcagtt | 1980 |
| tcttcatctt | taaagtgata | attttgccag | gcacagtggc | tcacacctgt | aatcccaaca | 2040 |
| ctttgggaga | ctgaggtggt | agatcatctg | agcccaggag | ttcgagacca | tcctgggcaa | 2100 |

```
catagtgaga ccctgtctga acaaaaaata aaataaaaaa ttatggtggc acatgcctgt    2160
gggctcagct actcagaaag ttgaggtaag gggatcactt gagccaggtg atcagggctg    2220
tagtgagttg tgattgcacc actgcactcc agcctgggca acagagcgag atcctgtctc    2280
aaaataaaaa taaataaata aaataataat tttaataact taccaggata tacacacatg    2340
cttaatgttc taataatgag tatcaggatg ggtatgggtg tcttagtctg ctttatgctg    2400
ctataacagg atgcttgtta taagagggc aatttataaa tagaaattaa tttctcacag    2460
tctaggagct gggaagtcca agatcgagtg gccagcatct atctggtgag tgccttcttt    2520
ctgcattaaa acatggcaga agacatcaca tgccagaaag agaagagaga gaaagagaaa    2580
gaggggtgga actcatcctt ttataaagaa cccactcctg agacaatggc actaatctat    2640
tcatgagggt ggtgccctg acccaaacaa tggcagcatc tcaccccacc tcccaacacc    2700
tccacattgg gggtcaagtt ttcaacagat gaacttgggg agacatattc aaaccataac    2760
agggagcaga ggctctgtga tgcctgtgtg ttggggcatc ccgaatccct tcactccaat    2820
ttgccatgcc cttttccatcc ccttgtctcc cacttcactg tcaccactgg aattcaagtc    2880
tccaggcagc atcttttgcc tgcattattg caataacaaa gtgctttctt tactctcctg    2940
caacaatcaa agcatgcaaa ttaacatacg ggtgagaaac caccctgcc cccaccccc    3000 ttcgctactc aggcaaagac ttttaaaata atgataacaa tgttgggggt ggggagcccc    3060 cttccccac agggcatgat tgtacactgg tatatttctg gaaagcaatt tagtaggaag    3120 tacttttga ttcttttttt ctttttttat tttatttat tttatttttt ttgagacgga    3180
gtctcgctct gtcacccagg ctggagtgca gtggcgtgat ctcggctcac tgcaagcttc    3240
acctcccggg ttcacgccat tctcctgcct cagcctcctg agtagctggg actacaggcg    3300
cccgccacca cgcccggcta atttttttt ttttttttgt attttagta gagacagggt    3360 ttcacggtgt tagccaggat ggtctcgatc tcctgacctc gtgatccacc cgcctcggcc    3420
tctcaaagtg ctgggattac aggcgtgagc caccgcgccc ggcctacttt tgattctac    3480 aggtccattt ttcaaaatac aatctaaaga aaaatcagtt ttggcacaaa actttgtta    3540 caaggctcct tatggtaata ttgtttctga tgaaagaaaa aagaagacag aaagaaagaa    3600
agaagaaaga agagaaagaa agagaaagaa agagaagaga aagaaagaag aaggaaggaa    3660
ggagagaagg aaagggagaa ggaagaagaa ggaaagaaaa actcagacat ccagcaggaa    3720
gcttggttaa ataaactgta gtagtccata ccttaaaatg ccattccttc actaaaaatg    3780
atgttgtagc tcagtagttt gtgcatcacg tgggaactgt tagaaatgca cattctgggg    3840
ccccatccca catctgattc agaaactctt ggggttggtt ggggtgggga ggttggggc    3900 gggaggtgga agcaatctgg gttttaataa accctccaag gcaattcaga gccatagctg    3960
tagaggacca tcgctaggga agttacgct gttaagtgag gaaaggttgg gaggcagtaa    4020
gcaggaacgt gcatcccca tatctgttat ctagagaaag gcacaaatag aaaaagtctg    4080
ggaggagttt atacccaggt gataacatcg acactctcta ggaggcagat tataaagttt    4140
tagagtaatt tcggtaattc atgttttcta aactagtcta caatgactat gtttgtgtaa    4200 aaagaaaga aaaaaacagt aatttatttt ttaatttaaa aaaaagtta aatgggacca    4260 agttgagagg agggtgtagg gaaggaggca gagagcccgc ctcgccgcga cagctttcac    4320
cccgggaaag ctgtgaggca ggaccgccca ggagacccgg ggccagtgga gtgggcagcg    4380
ccaggggtcc cggcgactca tctgatgtct agcaaggctt acgagggctt aaataataag    4440
```

```
cgaagagagt cagggcagat tccggaataa cttcactgct aagggtatca aatcctggaa    4500 tgggcaccttt ggagaggttt tctagccaag aacggacagc gggtgccagg aggggggtgga   4560 gtttcgccgg cccgcggaca gaggctgccg gatctcccga cccctccag caccgggact    4620 ccggggaggc tgcgcccgcg gcgggattcc cgcccctcgg agatgccgcg gggaccggcg    4680
gggcggggcc gggccgttgc taggggaggg gcggccaggc gcgcgaggaa cccagcgggc    4740
gaccgctaag cacactaggt tctccggctc cagctcctgc gccgcctgtt gctcgctcct    4800
ccgggcggtc gcttcccgcc cggtgcccag gggtaggcgg cccgagagcg cgcaggcagc    4860
cagcctcccg ccttcgtccc ctccccgtac cgcaggagcc ggtccgaggg gtccggagcg    4920
tccctgagag cgcggacccc ggcgagcagc ccagtgcacc cgggactgcg cgccgagacc    4980
cccggcgccg cgcggcgatg                                                5000

<210> SEQ ID NO 2
<211> LENGTH: 21
<212> TYPE: DNA
<213> ORGANISM: Homo sapiens

<400> SEQUENCE: 2
ttcggtttta gtttttgcgt c                                              21

<210> SEQ ID NO 3
<211> LENGTH: 21
<212> TYPE: DNA
<213> ORGANISM: Homo sapiens

<400> SEQUENCE: 3
aaccgactcc tacgatacga a                                              21
```

NON-INVASIVE DETECTION OF GASTRIC CANCER BY DETECTING THE METHYLATION OF REPRIMO-LIKE IN THE BLOOD

FIELD OF THE INVENTION

The invention aims at a non-invasive detection method for gastric cancer based on the detection of a molecular marker in blood. In particular, by detecting methylation in a specific region of the Reprimo-like gene (Gene ID: 388394, located at position 17q21.32 of the genome) in circulating DNA in peripheral blood.

BACKGROUND

Gastric cancer is the fifth most common cancer and the third leading cause of death in the world. Despite advances in its treatment, the prognosis is negative since it is frequently detected in advanced stages. When the disease is confined to the mucosa and submucosa layers of the stomach (early stages), the survival rate is 95% at 5 years. In contrast, when it extends to the muscularis propria or serous layers (advanced stages), patient survival drops substantially to 10 to 20% at 5 years.

Diagnosis of gastric cancer in the early stages is difficult, since most cases are asymptomatic until a very advanced stage.

There are several biomarkers that are directly detected in non-invasive samples to diagnose gastric cancer in an asymptomatic population. The best known is the marker of gastric atrophy (a precursor lesion of gastric cancer) called pepsinogen I/II. Gastric atrophy has a risk of developing gastric cancer at between 5 and 10%, which implies that these patients will require special surveillance with invasive methods such as radiology and endoscopy.

On the other hand, gastric atrophy, in addition to being the precursor lesion for gastric cancer, is a lesion associated with aging. Therefore, its predictive value is lost as the age of the population under evaluation increases.

In view of the need for early diagnostic methods to prevent the high mortality rate of advanced gastric cancers, it is necessary to seek new early diagnostic methods that are applicable to the asymptomatic population, in a rapid, non-invasive, effective and low-cost manner.

The invention provides a new early gastric cancer biomarker, which can be studied with non-invasive methods, such as a peripheral blood sample. Specifically, the invention aims to detect methylation in a specific region of the Reprimo-like gene (Gene ID: 388394, located at position 17q21.32 of the genome) in free DNA in plasma.

The Reprimo-like gene (RPRML) is part of the Reprimo gene (RPRM) family, which has been extensively studied as a potential biomarker in various types of cancer. The same inventors have studied and protected the use of the reprimo gene (RPRM) as a biomarker of gastric cancer, where the patent application WO2016205971 protects an ultrasensitive and specific method of detection of this biomarker, which can be applied to the blood tests of the patient, whose disclosure is incorporated herein by reference to the present invention.

Unlike Reprimo, the Reprimo-like gene has been studied very incipiently in terms of its function or utility as a biomarker. However, it has a more specific expression pattern than Reprimo, limited mainly to the stomach, brain and vasculature (Genotype-Tissue Expression database, www.gtexportal.org). The inventors have established the utility of RPRML as a biomarker since they have found that Reprimo-like is consistently silenced in gastric cancer, both in early and advanced stages. This silencing is given by methylation of its promoter region, which is detectable in plasma samples, allowing us to measure it as a liquid biopsy in a non-invasive, fast and inexpensive manner.

PRIOR ART

In 2010, Lin published the work "Reprimo-like is a P53 Responsive Gene Whose Promoter Methylation May Predict for Radiation Responsiveness in Pancreatic Cancer" (Lin et al., International Journal of Radiation Oncology Biology Physics; 78, 3; 5129; 2010; ISSN: 0360-3016.) Where it presents Reprimo-like as an alternative biomarker to Reprimo to evaluate in gastrointestinal tumors, particularly pancreatic. The results show that Reprimo-like is methylated at a low frequency (25% to 50%) compared to Reprimo (60% to 80%) in gastrointestinal (GI) tumors, where tumor biopsies are studied. The conclusion of this study is that the hypermethylation of the Reprimo-like promoter may be a marker for determining radiation sensitivity in patients with pancreatic cancer. Thus, Lin et al. Does not anticipate the correlation of methylation in the Reprimo-like promoter with an early detection of gastric cancer, and works with tumor biopsies, not with peripheral blood, so this document does not anticipate even itself, nor in combination with other documents, the subject matter of the invention.

Another document that could be considered prior art in this case is the international publication WO2012174256 (Arul et al., University of Michigan, 2012). This document studies 1,171 methylated genes in prostate cancer lines, among which is Reprimo-like, however, of these 1,171, only WFDC2, MAGI 2, MEIS2, NTN4, GPRCSB, C9orf125, FGFR2, AOXI, VAMPS, C14orf159, PPP1R3C, S100AJ6 and AMT are considered as prostate cancer markers (See claim 1 WO2012174256). That is to say, although Arul et al. Studied Reprimo-like and its methylation, they discarded it as a marker for prostate cancer.

In conclusion, the state of the art recognizes the existence of the reprimo-like gene and knows that it can be silenced by methylation of its promoter. However, it had not correlated Reprimo-like promoter methylation with early detection of gastric cancer, as is done in the present invention.

DESCRIPTION OF THE INVENTION

Figure 1:
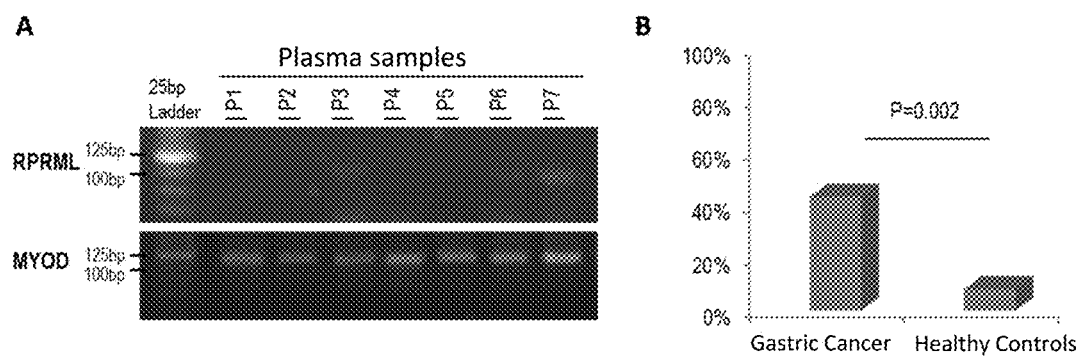
FIG. 1. Detection of Reprimo-like methylation in plasma samples. A) Representative image of an MSP assay used to detect Reprimo-like methylation (RPRML) in free DNA in plasma. The lower part of the figure shows the methylation of a reference gene (MYOD) used as a loading control. B) Graphic representation of the percentage of cases with positive methylation in plasma of patients with gastric cancer and healthy controls (p=0.002, Fisher's exact test).

The invention aims at a non-invasive method for the early diagnosis of gastric cancer, using as a biomarker the levels of methylation of the DNA sequence of the promoter of the Reprimo-like gene in plasma. The inventors have established the utility of Reprimo-like as a biomarker, and especially as a biomarker for the early detection of gastric cancer, since they have determined that Reprimo-like is consistently silenced in gastric cancer, both in incipient and advanced stages. This silencing is given by methylation of its promoter region, which is detectable in plasma samples, allowing us to measure it as a liquid biopsy in a non-invasive, fast and inexpensive way.

Specifically, the invention presented here is a method for the early detection of gastric cancer, by detecting the increase in DNA methylation of the promoter region of the Reprimo-like gene in samples obtained non-invasively, preferably in plasma. Thus, being a contribution to the early detection of gastric cancer, without invasive procedures, with rapid sample collection and delivery of results, and lower cost than technologies that employ diagnostic techniques which are invasive to human, and animal bodies in general.

As indicated, the Reprimo-like gene (RPRML) is part of the Reprimo gene family (RPRM), and is found at position 17q21.32 of the genome (Gene ID: 388394). The promoter region of RPRML is considered 5000 bp upstream of the start of translation (ATG) and is shown in SEQ ID No. 1.

The inventors have determined that Reprimo-like is silenced very early in tumors in gastric cancer and that it is inactivated by DNA methylation in its promoter region. Based on this result and on the need for a reliable biomarker, quick to quantify at low concentrations from non-invasively isolated samples, and at low cost for people; the method of the invention has been developed, which allows the development of gastric cancer to be detected early, since surprisingly the inventors have substantiated that establishing the degree of DNA methylation of the promoter region of the Reprimo-like gene in plasma, allows for the correlation of an increase of said degree of methylation within patients with gastric cancer compared to the healthy population.

In this way, the invention contributes to the state of the art, the detection of the methylated DNA of the promoter region of the Reprimo-like gene, as a biomarker of gastric cancer, in samples obtained non-invasively, preferably from plasma, where an increase in levels of such methylated DNA, is indicative of developing gastric cancer. While low circulating levels of methylated DNA of said promoter region of the Reprimo-like gene is indicative of the absence of disease at the time of analysis.

The invention thus provides new methods for the early diagnosis of gastric cancer characterized by being non-invasive, high precision, fast in delivering results and low purchasing and operating cost.

The method of detecting the methylated DNA sequence comprising the Reprimo-like gene expression promoter can be detected by any means available in the art, such as Polymerase Chain Reaction for methylated sequences (MSP), quantitative MSP, bisulfite sequencing (Methylseq), pyrosequencing, or molecular micromotors, for example.

In one embodiment, the invention employs specific methylation primers for PCR or MSP, which make it possible to specifically detect low levels of concentration of the methylated DNA sequence of the Reprimo-like gene promoter. If a PCR technique for methylated sequences is chosen to carry out the invention, the primers can be designed for any region of the promoter. All possible embodiments for the detection of the methylated sequence of this promoter are within the scope of the present invention. In a preferred embodiment, the methylation of the promoter region of RPRML can be evaluated by the Methylation Specific PCR (MSP) technique using the primers of the invention, which have the following sequence:

Sense primer: 5'-TTCGGTTTTAGTTTTTGCGTC-3' (SEQ ID No.2)
Antisense primer: 5'AACCGACTCCTACGATACGAA-3' (SEQ ID No.3)

It will be apparent to those skilled in the art that different pairs of primers can be designed to evaluate the methylation of this 5000 nucleotide region (SEQ ID No.1) or its complementary region. All of these embodiments are considered within the scope of the present invention.

A preferred embodiment of the invention is described below, without limiting the technical variants that a person skilled in the art can incorporate or modify, and which are within the scope of the inventive concept that is claimed in this application.

EXAMPLES

Example 1. Detection of Reprimo-Like Methylation in Plasma Samples

Plasma collection was carried out with conventional techniques, of which (0.5-1 ml) was used to extract DNA from 23 patients with gastric cancer and 36 healthy controls using the "QIAamp DNA Mini Kit" according to the suppliers' instructions. (QIAGEN, USA). The extracted DNA was dissolved in 20 µL TE buffer and bisulfite conversion was carried out using the reagents of the EZ DNA Methylation-Gold™ Kit (Zymo Research Corporation, Irvine, Calif., USA).

A specific PCR was carried out for the methylated DNA (MSP) of the Reprimo-like gene promoter, it was carried out according to the procedure of Zhengrong Li, et al., "Methylation-associated silencing of MicroRNA-335 contributes tumor cell invasion and migration by interacting with RASA1 in Gastric Cancer," American Journal of Cancer Research Vol. 4, issue 6, pp. 648-662, (Nov. 19, 2014), using the primers:

Sense primer: 5'-TTCGGTTTTAGTTTTTGCGTC-3' (SEQ ID No.2)
Antisense primer: 5'AACCGACTCCTACGATACGAA-3' (SEQ ID No.3)

In FIG. 1 A) you can see a representative image of one of the MSP assays used to detect Reprimo-like methylation (RPRML) in free DNA in plasma, the summary of the results is shown in FIG. 1 B) where The percentage of cases with positive methylation in plasma of patients with gastric cancer and healthy controls is represented, which was detected in 43.5% of the cases with cancer and only in 8.3% of the controls, obtaining a statistically significant difference with p=0.002 (Fisher's exact test).

Example 2. Correlation of Reprimo-Like Expression with Methylation

Figure 2:
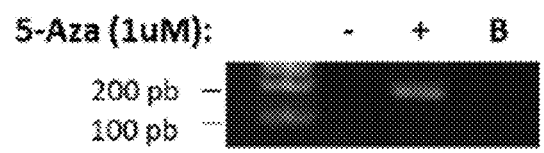
FIG. 2. Treatment with demethylating drug 5-Azacytidine (5-Aza) reactivates expression of RPRML in cell line SNU-16 at the mRNA level. (B=white). A gel is shown with the amplification of RPRML mRNA extracted from a culture of SNU-16 cells under normal conditions (−) where it is seen that there is no expression of the mRNA, and from the culture after treatment with 5-Aza (+), where the expression of the RPRML mRNA is seen.

The method of the invention is based on the fact that the methylation of free DNA in plasma is directly correlated with the methylation of DNA in the tumor and the consequent transcriptional silencing, which is why it is a method recognized as a true "liquid biopsy" of the tumor. In order to verify this correlation, a gastric cancer cell line SNU-16 was used, and the expression of the RPRML protein was measured under basal conditions and after treating the cells with the demethylating drug 5-Azacytidine (5-Aza). The mRNA level for this protein was measured in both situations. The results are shown in FIG. 2, where an increase in Reprimo-like mRNA is observed after treatment, that is to say, it is verified that its expression is regulated by methylation in gastric cancer, since treatment with a demethylating drug reactivates its expression.

The invention claimed is:

1. A method for detection of gastric cancer wherein the method comprises:
   collecting a plasma sample from a human subject, wherein the plasma sample is obtained in a non-invasive manner;
   extracting DNA from the plasma sample;
   performing a bisulfite conversion reaction on the extracted DNA;
   following the bisulphite conversion reaction, measuring, in the extracted DNA, the presence of aberrant DNA methylation in all or part of a promoter sequence of a Reprimo-like gene, as defined in SEQ ID No. 1, or its complementary sequence, using specific methylation primers having SEQ ID No. 2 for a sense primer and SEQ ID No. 3 for an antisense primer, where the presence of the aberrant DNA methylation is compared against a control sample corresponding to the absence of methylation in a healthy population.

2. A method for detection of gastric cancer according to claim 1 wherein measuring the presence of the aberrant DNA methlylation includes Polymerase Chain Reaction for methylated sequences (MSP).

* * * * *